Figure 1:
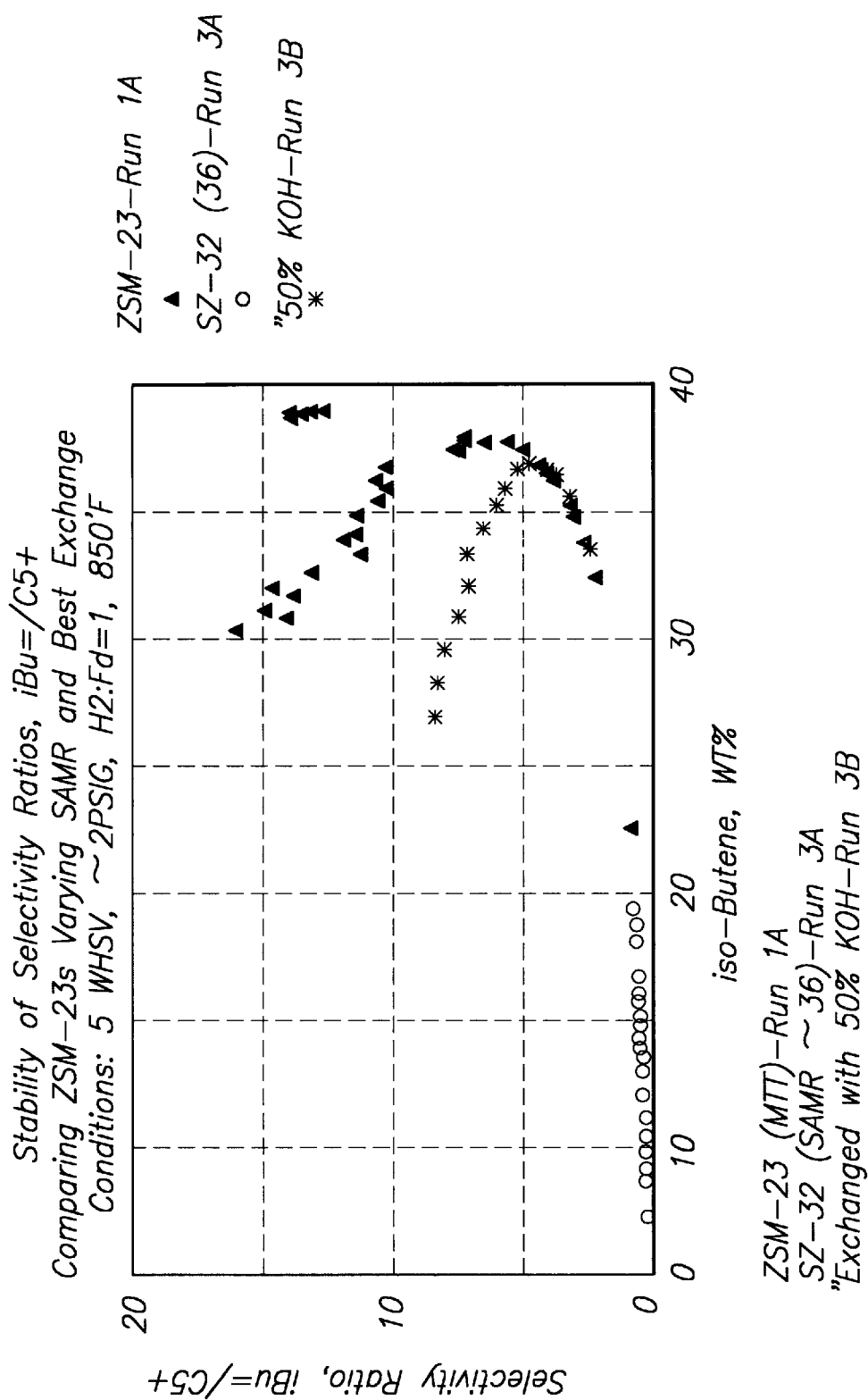

United States Patent [19]

Kluksdahl et al.

[11] Patent Number: 5,849,975

[45] Date of Patent: Dec. 15, 1998

[54] PROCESS FOR ISOMERIZATION OF NORMAL OLEFIN

[75] Inventors: Harris E. Kluksdahl, San Rafael; Lawrence W. Jossens, Albany; Thomas V. Harris, Benecia; Stacey I. Zones, San Francisco, all of Calif.

[73] Assignee: Chevron U.S.A. Inc., San Francisco, Calif.

[21] Appl. No.: 782,015

[22] Filed: Jan. 7, 1997

[51] Int. Cl.$^6$ ...................................................... C07C 5/27
[52] U.S. Cl. .............................. 585/671; 568/697; 502/64
[58] Field of Search ............................ 585/671; 568/697; 502/64

[56] References Cited

U.S. PATENT DOCUMENTS

| | | | |
|---|---|---|---|
| 3,104,249 | 9/1963 | Clauss et al. | 260/429.5 |
| 3,104,251 | 9/1963 | Foster et al. | 260/448 |
| 3,104,253 | 9/1963 | Rectz | 260/461 |
| 4,076,842 | 2/1978 | Plank et al. | 423/328 |
| 4,481,177 | 11/1984 | Valyocsik | 423/329 |
| 5,053,373 | 10/1991 | Zones | 502/64 |
| 5,491,276 | 2/1996 | O'Young et al. | 585/671 |

OTHER PUBLICATIONS

"Note, Skeletal Isomerization of 1–Butene in 10–Member Ring Zeolite Catalysts", *Journal of Catalysis* 151:, 467–469 (1995).

"Notes, Catalysis by Crystalline Aluminosilicates: Characterization of Intermediate Pore–Size Zeolites by the 'Constraint Index'", *Journal of Catalysis* 67, 218–222 (1981).

*Primary Examiner*—Gary Geist
*Assistant Examiner*—Sreeni Padmanabhan
*Attorney, Agent, or Firm*—Timothy J. Hadlock

[57] ABSTRACT

A process for skeletal isomerization of light normal $C_{4-6}$ olefins to iso-olefins by contacting a hydrocarbon stream containing $C_{4-6}$ normal olefins under isomerization conditions with a SSZ-32 zeolite catalyst.

20 Claims, 1 Drawing Sheet

PROCESS FOR ISOMERIZATION OF NORMAL OLEFIN

I. FIELD OF THE INVENTION

This invention relates to a process for skeletal isomerization of a light normal olefin, especially of normal butene, using a medium pore aluminosilicate zeolite catalyst, SSZ-32.

II. BACKGROUND OF THE INVENTION

Conversion of $C_{4-6}$ normal olefins to the corresponding iso-olefins is important for preparing feed stocks for production of oxygenates, alkylates, and specialty petrochemicals. There are only a limited number of commercial processes currently available. Processes which use amorphous catalysts require frequent regeneration due to a short catalyst life. Zeolites offer the potential of shape selectivity to make the desired product, and this often also results in extended catalyst life.

In recent years, several commercial processes became available utilizing various zeolite catalysts for the conversion of normal butene to iso-butene. See generally, Note, Skeletal Isomerization of 1-Butene on 10-Member Ring Zeolite Catalysts, Journal of Catalysis 151, 467–469 (1995). Performance varies from catalyst to catalyst. There remains, however, a need for additional zeolite catalyst processes. Additional zeolite catalyst processes provide an opportunity for tailoring the choice of catalyst to the particular feed stream.

New catalysts processes which can produce the same iso-butene product at a lower catalyst price allow the iso-butene manufacturer to better compete in the marketplace. The acidity and crystal size are important parameters in the performance of the zeolite. Small crystals are desirable in may applications. The addition of aluminum oxide has been shown to reduce crystal size in certain zeolites. However, it has been difficult to obtain Si:Al ratios oxide greater than about 20:1 to less than 40:1. For these reasons, it would be desirable to have a new catalyst process for the skeletal isomerization of normal butene to iso-butene.

The present invention provides such a zeolite catalyst. A medium pore aluminosilicate zeolite, SSZ-32, is the catalyst used in the present process. The zeolite used in the present process has essentially the same X-ray diffraction pattern as ZSM-23, described in U.S. Patent No. 4,076,842. In the present invention, the aluminum content is higher than in ZSM-23. The X-ray diffraction lines are quite broad due to the very small crystal size.

III. SUMMARY OF THE INVENTION

In accordance, therefore, with the present invention, a process is set forth for skeletal isomerization of light normal $C_{4-6}$ olefins to iso-olefins, particularly normal butene to iso-butene. The process includes contacting a hydrocarbon stream containing $C_{4-6}$ normal olefins at isomerization conditions with a catalyst including a zeolite having a mole ratio of silicon oxide to aluminum oxide greater than about 20:1 to less than 40:1, and having the X-ray diffraction lines of Table 1.

IV. BRIEF DESCRIPTION OF THE DRAWINGS

FIG. 1 depicts experimental test results associated with the experiment described in the Experiment Section.

V. DETAILED DESCRIPTION OF THE INVENTION

The present process relates to skeletal isomerization of light normal $C_{4-6}$ olefins to the iso-olefins by contacting a hydrocarbon stream containing $C_{4-6}$ normal olefins with an SSZ-32 zeolite.

A. Hydrocarbon Feed Stream

The feed stream is a hydrocarbon stream containing at least one $C_{4-6}$ normal olefin, particularly normal butene. Normal butene as used in this specification and appended claims shall mean all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40–60 weight percent normal butenes. A methyl-tert-butyl ether unit effluent typically contains 40–100 weight percent normal butene. The feed stream preferably contains at least about 40 weight percent normal butene, more preferably at least about 65 weight percent normal butene. The terms iso-olefin and methyl branched iso-olefin may be used interchangeably in this specification and appended claims.

B. SSZ-32

The zeolite useful in the present process is termed SSZ-32. Its composition and method of manufacture is disclosed in co-assigned U.S. Pat. No. 5,053,373, which is incorporated herein by reference. SSZ-32 zeolites, as synthesized, have a crystalline structure whose X-ray powder diffraction pattern shows the following characteristic lines:

TABLE 1

| d/n | Int. $I/I_o$ |
|---|---|
| 11.05 | 26 |
| 10.05 | 10 |
| 7.83 | 17 |
| 4.545 | 71 |
| 4.277 | 71 |
| 3.915 | 100 |
| 3.726 | 98 |

The X-ray powder diffraction patterns were determined by standard techniques. The radiation was the K-alpha/doublet of copper and a scintillation counter spectrometer with a strip-chart pen recorder was used. The peak heights 1 and the positions, as a function of 2P where P is the Bragg angle, were read from the spectrometer chart. From these measured values, the relative intensities, 100 $1/1_o$, where $1_o$ is the intensity of the strongest line or peak, and d, the interplanar spacing in Angstroms corresponding to the recorded lines, can be calculated. The X-ray diffraction pattern of Table 1 is characteristic of novel SSZ-32 zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-alumina mole ratio from sample to sample.

Calcination can also cause minor shifts in the X-ray diffraction pattern. Notwithstanding these minor perturbations, the basic crystal lattice structure remains unchanged. Methods of preparing SSZ-32 zeolites are disclosed in U.S. Pat. No. 5,053,373, the disclosure of which is incorporated herein by reference.

The synthetic zeolites can be used as synthesized or can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:alumina mole ratio. At least a portion of the acid sites of the zeolite preferably are "neutralized" or ion exchanged with a metal cation. The amount of ion-exchange is an amount sufficient to reduce the acidity along the walls of the pores of the zeolite. The amount of ion-exchange is from about 5% to about 90%, preferably at least 20%, 25%, 50%, 60%, or 75%. Replacing cations are selected from metals which will have a neutralization effect but not a catalytic effect. Typically, the metals are selected from Groups 1 and 2' of the periodic table, individually or in mixtures. The metal cation sources are any conventional source and in a preferred embodiment of the process the metal cation sources are KOH, CsOH, or $Ca(NO_3)_2$.

The metal components can be exchanged into the zeolite. The zeolite can also be impregnated with the metals, or the metals can be physically intimately admixed with the zeolite using standard methods known to the art. And, the metals can be occluded in the crystal lattice by having the desired metals present as ions in the reaction mixture from which the SSZ-32 zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place either before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to 820° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

It is preferred that relatively small crystal size zeolite be utilized in practicing the invention. Preferably, the average crystal size is not greater than about 0.5 microns, more preferably no more than about 0.1 microns, and still more preferably not more than about 0.05 microns.

The shape selectivity of SSZ-32 is manifested by Constraint Index values (as defined in J. Catalysis 67, page 218), after calcination and in the hydrogen form, of preferably greater than 12, and more preferably 13 or greater. Determination of Constraint Index is also disclosed in U.S. Pat. No. 4,481,177.

The "constraint index" is determined by passing continuously a mixture of an equal weight of normal hexane and 3-methylpentane over a sample of zeolite at atmospheric pressure according to the following procedure. A zeolite sample is prepared in the form of pellets. The pellets are lightly crushed, and the 20–40 mesh fraction is dried in flowing air at 1000° F. (about 538° C.) for at least 30 minutes.

A reactor tube is charged with 0.47 grams of the dried zeolite sample. Helium at 9.4 cc/min is introduced to the catalyst charge, and the charge is heated at 800° F. A 1:1 weight ratio blend of normal hexane and 3-methylpentane is then passed over the zeolite at 8 μl/min. Effluent samples are analyzed by on-line gas chromatography to determine the fraction remaining unchanged for each of the two hydrocarbons. The "constraint index" is calculated as follows:

$$Constr.\ Index = \frac{\log_{10}(\text{fraction of } n\text{-hexane remaining})}{\log_{10}(\text{fraction of 3-methylpentane remaining})}$$

The constraint index for the zeolite in the process of the invention is optionally above 12.

The aluminosilicate can be formed into a wide variety of physical shapes. Generally speaking, the zeolite can be in the form of a powder, a granule, or a molded product, such as an extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or dried or partially dried and then extruded. The zeolite can be composited with other materials such as, e.g., silica, silica-alumina, alumina, bentonite, kaolin, bentonite with alumina, montmorillonite, attapulgite, titania, or zirconia.

The binders may be chosen for being resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes.

Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Georgia and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the SSZ-32 zeolites can be composited with porous matrix materials and mixtures of matrix materials such as silica, alumina, titania, magnesia, silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The SSZ-32 zeolites can also be composited with other zeolites such as synthetic and natural faujasites (e.g., X and Y), erionites, and mordenites. They can also be composited with purely synthetic zeolites such as those of the ZSM series. The combination of zeolites can also be composited in a porous inorganic matrix.

C. Process Conditions

The process is carried out under isomerization conditions. The hydrocarbon feed is contacted in a vapor phase with the Zeolite SSZ-32. The process of the present invention is carried out generally at a temperature from about 625° F. to about 950° F., for butenes, preferably from about 700° F. to about 900° F., and about 350° F. to about 650° F. for pentenes and hexenes. The pressure ranges from subatmospheric to about 200 psig, preferably from about 15 psig to about 200 psig, and more preferably from about 1 psig to about 150 psig.

The liquid hourly space velocity during contacting is generally from about 0.1 to about 50 hr$^{-1}$, based on the hydrocarbon feed, preferably from about 0.1 to about 20 hr$^{-1}$, more preferably from about 0.2 to about 10 hr$^{-1}$, most preferably from about 1 to about 5 hr$^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

During the process, some coke will be formed on the catalyst. Therefore, it is advantageous to regenerate the catalyst. The catalyst can be regenerated by subjecting it to heat treatment with air, nitrogen/oxygen gas mixture, or hydrogen. A continuous regeneration, similar to the regeneration carried out in a fluidized catalyst cracking process, may be useful.

D. Further Processing

In one embodiment of the invention, the isomerization effluent containing a $C_{4-6}$ iso-olefin is passed to an etherification zone containing an alcohol and an etherification catalyst to form a reaction product containing an alkyl-tert-alkyl-ether. This is followed by recovering the alkyl-tert-alkyl-ether reaction product. In one preferred embodiment of the invention, the $C_{4-6}$ iso-olefin contains iso-butene and the reaction product contains methyl-tert-butyl-ether.

VI. EXAMPLES

The invention will be further clarified by the following examples, which are intended to be purely exemplary of the invention.

A. Introduction

The zeolite SSZ-32 of the process of the invention was compared to existing zeolite processes for isomerization of normal butene to iso-butene. For SSZ-32, various ion exchange/neutralizing agents of acid site were compared for relative performance.

B. Experimental Method

The experimental runs were conducted in a micro-reactor. The experimental runs tested a ZSM-23 zeolite, a Theta-1 zeolite, and a SSZ-32 zeolite of the process of the invention. For each run, indicated in Table 2 below, the zeolite was packed column of approximately one and one-half feet in length, having a one-quarter inch inner diameter and a three eighths inch outer diameter. The physical form of the zeolite was pellitized powder. The pellitized powder was formed by pressure forming without the aid of any binder material, although in commercial use a binder is typically necessary for containment of the fine powder zeolite. The mesh size was from 24 to 42.

The fixed zeolite bed occupied approximately the center two inches of the column with packing material above and below the bed. The packing served to contain the zeolite and the upper packing served to preheat the feed stream. The hydrocarbon feed of substantially pure normal butene and hydrogen were passed through the column in a downflow manner. The molar ratio of normal butene to hydrogen was about 1:1.

The column is placed in a heating furnace to bring the zeolite bed to a temperature of about 850° F. All the runs took place at this temperature except for run 3C which took place at about 950° F. All runs were at ambient pressure.

The product stream from the bottom of the column was connected to a GC for periodic analysis of the product. GC analysis was conducted approximately every six hours. The portion of the product stream not sent to the GC was condensed and collected. GC analysis determined the concentration of iso-butene and for $C_{5+}$ material. The $C_{5+}$ material is mostly undesirable oligimerized by-products. The concentration of iso-butene and $C_{5+}$ material plotted against time as shown in FIG. 1.

The duration of the runs was from start until performance peaked over 30% and then fell back below 30% iso-butene production. The time to decline to 30% iso-butene for the three runs ranged from 300 to 500 hours.

C. Results

The results are presented in Table 2 below:

TABLE 2

| Run # | Catalyst[2] | Acid-Site Neutralization | Performance[3] |
|---|---|---|---|
| 1A | ZSM-23 | MTT, $SiO_2/Al_2O_3$ = 200 | Good |
| 1B | ZSM-23 | 50% exchange with KOH | Poor |
| 1C | ZSM-23 | 25% exchange with LiOH | Poor |
| 2 | Theta-1 | None | Good |
| 3A | SSZ-32 | MTT, $SiO_2/Al_2O_3$ = ~36 | Poor |
| 3B | SSZ-32 | 50% exchange with KOH | Good |
| 3C | SSZ-32 | 25% exchange with CsOH | Good |
| 3D | SSZ-32 | 50% exchange with LiOH | Fair |
| 3E | SSZ-32 | 75% exchange with KOH | Poor |
| 3F | SSZ-32 | 10% exchange with KOH | Poor |
| 3G | SSZ-32 | 50% exchange with CsOH | Poor |
| 3H | SSZ-32 | 50% exchange with $Ca(NO_3)_2$ | Poor |

[2]Each zeolite was an MTT zeolite except for Run 2 which was a TON zeolite.
[3]Good = sustained 35–40% iso-butene production with less than 5% $C_{5+}$ production. Fair = Rapidly declining iso-butene production after achieving 35%. Poor = Less than 30% iso-butene production with greater than 10% $C_{5+}$ production.

As shown in above Table 2, in runs 3B and 3C, the performance of SSZ-32 zeolite exchanged with KOH and CsOH, respectively, produced good results comparable to that of ZSM-23 zeolite in run 1A and Theta-1 in run 2. Thus, these exchanged versions of SSZ-32 zeolite offer competitive performance against existing zeolite normal butene isomerization processes.

FIG. 1 plots iso-butene production on the X-axis and iso-butene production divided by $C_{5+}$ production on the Y-axis. The iso-butene and $C_{5+}$ production are calculated on a weight basis. The weight percent basis for production of iso-butene is based on the total weight of the isomerization unit effluent.

Results from runs 1A, 3A, and 3B are plotted. The circle plotted line shows SSZ-32 without any ion-exchange. The results are poor as iso-butene production is low both on an absolute basis and relative to production of $C_5$+ materials. The star plotted line shows the SSZ-32 having been ion-exchanged at a level of 50% with KOH. A dramatic improvement in performance is shown. The ion-exchanged SSZ-32 gives sustained good performance of over 30 weight percent iso-butene production. The triangle plotted line is ZSM-23 to use as a comparison. Accordingly, ion-exchanged SSZ-32 provides competitive performance for isomerization of normal butene to iso-butene.

What is claimed is:

1. A process for skeletal isomerization of normal butene to iso-butene said process comprising:
   a. contacting a hydrocarbon stream containing at least 40 weight percent normal butene at a temperature of from about 700° F. to about 900° F., a pressure of from about 1 psig to about 150 psig, and a liquid hourly space velocity from about 0.1 to about 5 hr$^{-1}$ with a catalyst comprising a zeolite having a mole ratio of silicon oxide to aluminum oxide greater than about 20:1 to less than 40:1, having a crystallite size not greater than about 0.5 microns, having at least a portion of its acid sites ion-exchanged with an alkali metal cation, and having the following X-ray diffraction lines:

| d/n | Int. I/I$_o$ |
|---|---|
| 11.05 | 26 |
| 10.05 | 10 |
| 7.83 | 17 |
| 4.545 | 71 |
| 4.277 | 71 |
| 3.915 | 100 |
| 3.726 | 98 | thereby producing an isomerization effluent containing iso-butene;
   b. passing said isomerization effluent containing iso-butene to an etherification zone containing an alcohol and an etherification catalyst to form a reaction product comprising methyl-tert-butyl-ether; and
   c. recovering said methyl-tert-butyl-ether reaction product.

2. A process for skeletal isomerization of a $C_{4-6}$ normal olefin to its corresponding methyl branched iso-olefin, said process comprising contacting a hydrocarbon stream containing at least one $C_{4-6}$ normal olefin under isomerization conditions with a catalyst comprising a zeolite having a mole ratio of silicon oxide to aluminum oxide greater than about 20:1 to less than 40:1, and having the following X-ray diffraction lines:

| d/n | Int. I/I$_o$ |
|---|---|
| 11.05 | 26 |
| 10.05 | 10 |
| 7.83 | 17 |
| 4.545 | 71 |
| 4.277 | 71 |
| 3.915 | 100 |
| 3.726 | 98. |

3. The process according to claim 2 wherein the hydrocarbon stream contains at least 40 weight percent normal butene.

4. The process according to claim 3 wherein the hydrocarbon stream contains at least 65 weight percent normal butene.

5. The process according to claim 2 wherein a portion of the acid sites of the zeolite are ion-exchanged with a Group 1 or 2 metal cation source.

6. The process according to claim 5 wherein said metal cation source is selected from the group consisting of KOH, CsOH, Ca(NO$_3$)$_2$, and mixtures thereof.

7. The process according to claim 6 wherein said alkali metal source consists essentially of KOH.

8. The process of claim 5 wherein said zeolite is combined with a binder selected from the group consisting of silica, silica-alumina, alumina, bentonite, kaolin, bentonite with alumina, montmorillonite, attapulgite, titania, zirconia, and mixtures thereof.

9. The process according to claim 2 wherein said contacting is carried out at a temperature of from about 625° F. to about 950° F., a pressure of from about 15 psig to about 200 psig, and a liquid hourly space velocity from about 0.1 to about 50 hr$^{-1}$.

10. The process according to claim 9 wherein said temperature is from about 700° F. to about 900° F.

11. The process according to claim 9 wherein the liquid hourly space velocity is from about 0.1 to about 5 hr$^{-1}$.

12. The process according to claim 2 wherein the zeolite has a crystallite size not greater than about 0.5 microns.

13. The process according to claim 2 wherein the zeolite has a constraint index of greater than 12.

14. The process of claim 5 further comprising passing said isomerization effluent containing a $C_{4-6}$ iso-olefin to an etherification zone containing an alcohol and an etherification catalyst to form a reaction product comprising an alkyl-tert-alkyl-ether; and recovering said alkyl-tert-alkyl-ether reaction product.

15. The process according to claim 14 wherein said $C_{4-6}$ iso-olefin comprises iso-butene and said reaction product comprises methyl-tert-butyl-ether.

16. A process for skeletal isomerization of a $C_{4-6}$ normal olefin to its corresponding methyl branched iso-olefin, said process comprising:
   a) contacting a hydrocarbon stream containing at least one $C_{4-6}$ normal olefin under isomerization conditions with a catalyst comprising a zeolite having a mole ratio of silicon oxide to aluminum oxide greater than about 20:1 to less than 40:1, and having the following X-ray diffraction lines:

| d/n | Int. I/I$_o$ |
|---|---|
| 11.05 | 26 |
| 10.05 | 10 |
| 7.83 | 17 |
| 4.545 | 71 |
| 4.277 | 71 |
| 3.915 | 100 |
| 3.726 | 98 | thereby producing an isomerization effluent containing a $C_{4-6}$ iso-olefin;
   b) passing said isomerization effluent containing a $C_{4-6}$ iso-olefin to an etherification zone containing an alcohol and an etherification catalyst to form a reaction product comprising an alkyl-tert-alkyl-ether; and
   c) recovering said alkyl-tert-alkyl-ether reaction product.

17. The process according to claim 16 wherein said $C_{4-6}$ iso-olefin comprises iso-butene and said reaction product comprises methyl-tert-butyl-ether.

18. The process according to claim 17 wherein said contacting is carried out at a temperature of from about 625° F. to about 950° F., a pressure of from about 15 psig to about 200 psig, and a liquid hourly space velocity from about 0.1 to about 50 hr$^{-1}$.

19. The process according to claim 18 wherein the zeolite has a crystallite size not greater than about 0.5 microns.

20. The process according to claim 17 wherein the zeolite has a constraint index of greater than 12.

* * * * *